US006555830B1

(12) United States Patent
Mankos et al.

(10) Patent No.: US 6,555,830 B1
(45) Date of Patent: Apr. 29, 2003

(54) SUPPRESSION OF EMISSION NOISE FOR MICROCOLUMN APPLICATIONS IN ELECTRON BEAM INSPECTION

(75) Inventors: Marian Mankos, San Francisco, CA (US); Tai-Hon Philip Chang, Foster City, CA (US); Kim Y. Lee, Fremont, CA (US); Ming Yu, Fremont, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/638,376

(22) Filed: Aug. 15, 2000

(51) Int. Cl.$^7$ .............................. G21G 5/00; G21K 5/10
(52) U.S. Cl. ................... 250/492.2; 250/250; 250/310; 250/311; 250/492.21
(58) Field of Search .............................. 250/492.2, 310, 250/311, 492.21

(56) References Cited

U.S. PATENT DOCUMENTS

| | | | | |
|---|---|---|---|---|
| 3,946,268 A | * | 3/1976 | Welter | 315/382 |
| 4,321,510 A | * | 3/1982 | Takigawa | 315/382 |
| 4,337,422 A | * | 6/1982 | Veneklasen | 315/383 |
| 4,427,886 A | * | 1/1984 | Martin et al. | 250/310 |
| 4,695,773 A | * | 9/1987 | Veneklasen et al. | 315/382 |
| 4,937,458 A | * | 6/1990 | Fujikura | 250/492.2 |
| 4,990,778 A | | 2/1991 | Norioka | |
| 5,969,355 A | * | 10/1999 | Fujii et al. | 250/309 |
| 5,993,636 A | * | 11/1999 | Terui et al. | 205/640 |

FOREIGN PATENT DOCUMENTS

| | | | |
|---|---|---|---|
| JP | 62093848 A | 4/1987 | |
| JP | 02262228 A | 10/1990 | |
| WO | WO 0160456 A | 8/2001 | |

* cited by examiner

Primary Examiner—Jack Berman
Assistant Examiner—K. Fernandez
(74) Attorney, Agent, or Firm—Jung-hua Kuo

(57) ABSTRACT

The microcolumn configuration of the present invention provides for emission noise reduction through the use of a screened beam-limiting aperture for monitoring the electron beam current. This novel approach utilizes a screening aperture located between the emitter and the beam-limiting aperture, which screening aperture collects most of the current transmitted by the first lens of the electron beam column. In order to achieve good noise suppression, the screening aperture should let through only the portion of the beam where the electrons are correlated. The current collected by the beam-limiting aperture is then used as a reference signal in the image processing. The elimination of this noise increases the detection sensitivity of an inspection tool. This reduces the total number of required pixels and therefore increases the throughput of the tool.

18 Claims, 2 Drawing Sheets

SUPPRESSION OF EMISSION NOISE FOR MICROCOLUMN APPLICATIONS IN ELECTRON BEAM INSPECTION

FIELD OF THE INVENTION

This invention relates to an electron beam inspection system using a field emission electron gun and a method and apparatus for measuring and correcting for the effect of beam current noise on the scanned electron image.

BACKGROUND OF THE INVENTION

In scanning electron beam inspection systems, defects are detected by comparing the signals from corresponding image pixels in the tested chip (die) and the reference standard. The reference standard may be an electronic database in which case the inspection is called die-to-database inspection, or the reference may be another test die, in which case the inspection is called die-to-die inspection. A defect is found when the signals between the die and the reference differ by more than a given detection threshold.

Field emission electron guns provide a suitable electron source for such scanning electron beam inspection systems. In a field emission electron gun, a voltage potential is applied between an emitter tip and the target. The electrostatic field present at the emitter tip of a field emission source is very high as a consequence of the small dimensions of the tip. This very high electrostatic field ($\sim 10^9$ V/m) causes electrons to be emitted from the tip, which electrons then migrate to the target.

In inspection systems with cold field or Schottky emission electron sources, a false defect may be caused by random spikes in the electron beam current, i.e. emission noise. In field emission sources, emission noise is a serious problem. Such emission noise does not occur in thermionic and $LaB_6$ electron emission sources; however thermionic emission sources have much lower brightness than field emission sources.

In field emission sources the effect of emission noise is independent from and additional to the effect of the beam dependent quantum shot noise. The quantum shot noise depends upon the total number of detected electrons, and its effect can be decreased by increasing the total beam current. Emission noise is caused by microscopic changes in the emission properties of a field emission or Schottky emitter tip, which results in a sudden change in the emitted beam current or a short current pulse. Although the emitter tip is placed in a high quality vacuum, one significant cause of such emission noise is the presence of residual gas. Gas molecules that remain may become ionized near the emitter tip. In turn such ionized gas molecules interact with the emitting surface of the emitter tip and give rise to random fluctuations in the beam current.

Typically a ZrO Schottky emitter, for example, may be subject to emission noise in the range of 1.5%, and this cannot be reduced by increasing the beam current. The emission noise may manifest itself in scanned electron images as an artificial defect. In imaging applications such as SEM (scanning electron microscopy) or metrology, these artificial defects can be averaged out by multiple pass averaging. However, multipass averaging is not desirable for inspection systems, since such averaging significantly increases the required inspection time and accordingly decreases throughput.

The purpose of the present invention is to reduce or eliminate the spurious effects of emission noise on the scanned electron images. The emission noise randomly increases or decreases the emitted electron beam and may manifest itself in scanned electron images as an artificial defect. The elimination of this noise both increases the detection sensitivity of an inspection tool and its throughput.

SUMMARY OF THE INVENTION

In one class of embodiments, the invention is an apparatus whose column configuration provides for emission noise reduction through the use of a beam-limiting element (having a beam-limiting aperture) for monitoring the electron beam current, and a screening element (having a screening aperture) positioned between the beam-limiting element and an electron source (emitters). The screening element collects most of the current transmitted from the emitter (e.g., most current transmitted by the first lens of the electron beam column). In order to achieve good noise suppression, the screening aperture should let through (to the beam-limiting element) only the portion of the beam where the electrons are correlated. The preferred implementation of this invention is the electron beam microcolumn; however the invention is also applicable to conventional columns operating at higher beam energies such as 10–100 kV.

In another class embodiments, the present invention is a method for emission noise reduction through the use of a screened beam-limiting aperture for monitoring the electron beam current. This novel method utilizes a screening aperture located between the emitter and the beam-limiting aperture, which screening aperture collects most of the current transmitted by the first lens of the electron beam column. In order to achieve good noise suppression, the screening aperture should transmit only the portion of the beam where the electrons are correlated.

According to the present invention, the current collected by the beam-limiting aperture is used as a reference signal in the image processing to correct for the effect of the emission noise. The elimination of noise (by processing the secondary electron data from the target using the reference signal) increases the detection sensitivity of an inspection tool. This reduces the total number of required pixels per substrate and therefore increases the throughput of the tool.

DETAILED DESCRIPTION OF THE INVENTION

Figure 1:
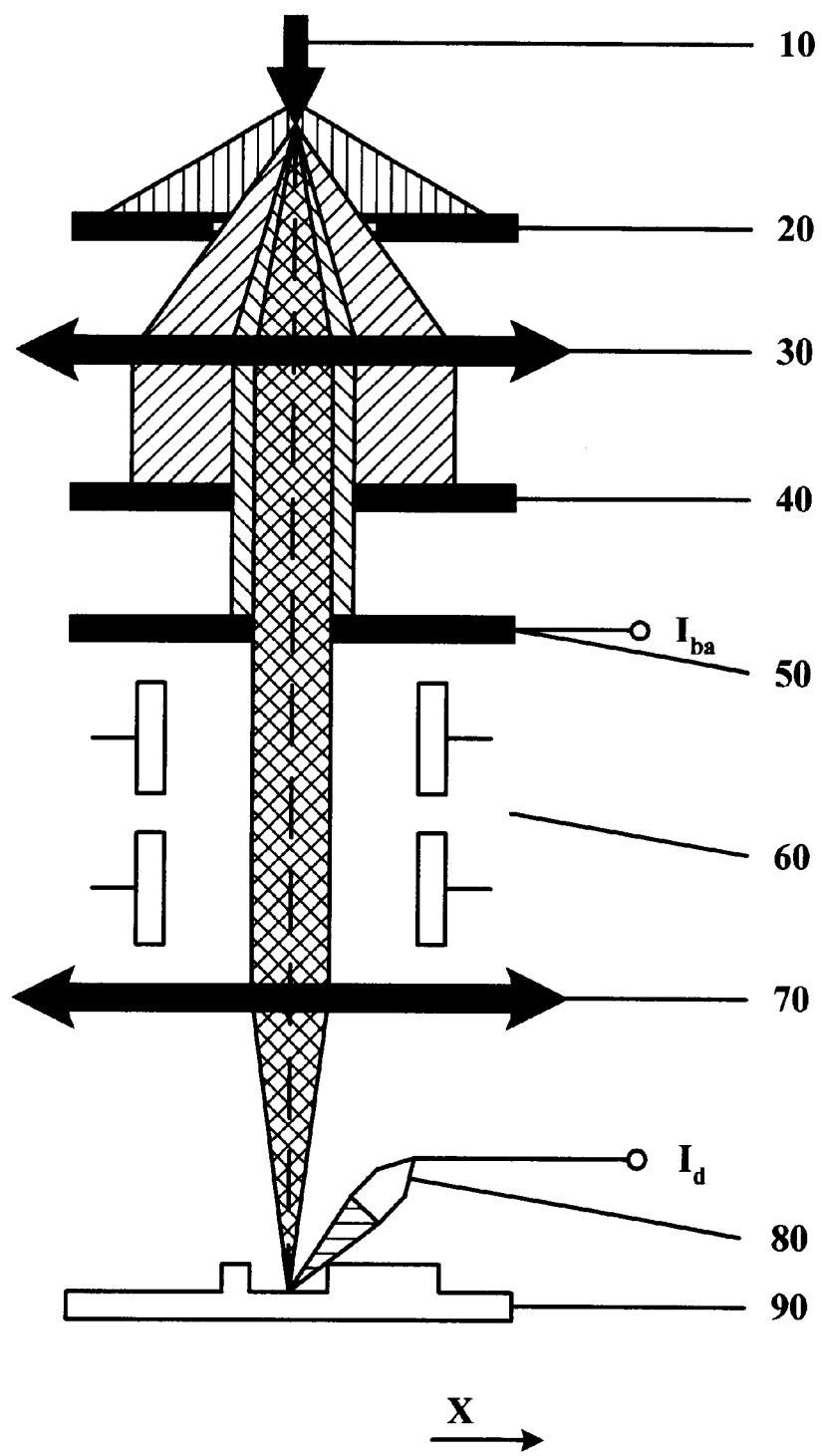
FIG. 1 is a cross-sectional view of an apparatus (including a diagram of the electron beam configuration) according to the present invention.

The principle of the emission noise reduction technique is shown in FIG. 1. The primary electrons are extracted from the Schottky emitter 10, focused by the source lens 30, accelerated to a final beam voltage of 1 keV and refocused with the final lens 70 onto the sample 90. As is known in the art, the electron-optical lenses may be either electrostatic lenses, magnetic lenses, or combination of the two. When a periodic voltage is applied to the deflection plates 60, the focused beam is swept across the sample 90 and generates secondary electrons. (As is known in the art, deflection coils could be used in place of the deflection plates.) Secondary electrons which escape from the sample surface strike the detector 80 and contribute to the signal $I_d$ which is used to create a secondary electron image.

However, only a small fraction of the emitted electrons hit the sample. The majority of the emitted electron current $I_e$, typically 50–200 μA, is collected by the extraction electrode 20 (which has an extraction electrode aperture extending through it). A small portion of the electron current, typically 100–300 nA, passes through the first lens 30. In a conventional set-up, the majority of this current is collected by the beam-limiting element 50 (having a beam-limiting aperture extending through it), and only a small fraction $I_b$, typically 1–50 nA, is utilized for imaging. The novel approach of the present invention utilizes a screening element 40 (having a screening aperture extending through it) located between the emitter 10 and the beam-limiting aperture 50, which screening aperture 40 collects most of the current transmitted by the first lens 30. Only a small fraction $I_{ba}$ of the electron current, approximately 1–10%, is collected by the beam-limiting aperture 50. (As used herein, references to the "beam-limiting aperture" and "screening aperture" should be understood to encompass the blocking or truncating structure that defines the aperture.) In order to achieve good noise suppression, the screening aperture 40 should let through only a portion of the beam in which the electrons are correlated. For electron emission along the axis of a Schottky emitter, the electrons are correlated within an emission half cone angle a given approximately by $$\alpha = \frac{2}{\sqrt{\pi}} \sqrt{\frac{kT}{\Phi}}$$

where T is the tip temperature, k is Boltzmann's constant and Φ is the electron energy. At 1800K, α is 14 mrad for 1 kV electrons, which is more than typically used in the microcolumn operation (5–10 mrad). The current $I_{ba}$ collected by the beam-limiting aperture 50 is then used as a reference signal in the image processing. Specifically, current measuring circuitry coupled to the beam-limiting aperture 50 measures the portion of the electron beam that is blocked.

Figure 2:
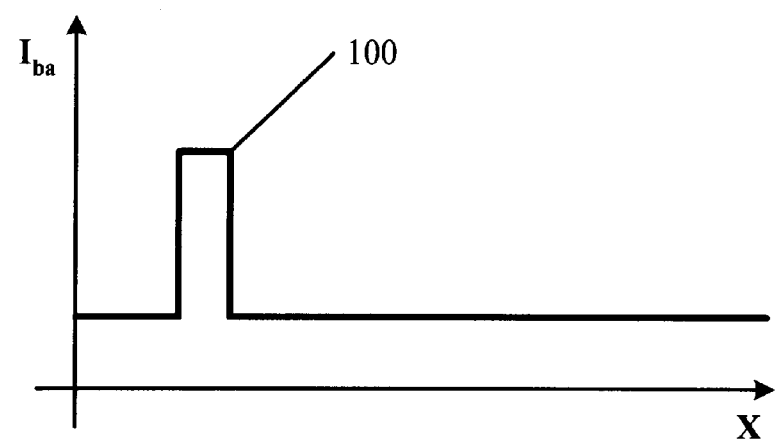
FIG. 2 is a set of three graphs showing an example of the removal of the effect of emission noise from data acquired using the electron beam configuration of FIG. 1. The top graph shows a current $I_{ba}$ collected by the screened beam-limiting aperture 50 while the electron beam $I_b$ is scanned (for example along the x-axis) across the sample 90 and contains an emission noise peak 100. The middle graph shows a secondary electron signal $I_d$ from the electron detector 80 and includes the emission noise peak 110, superimposed on the imaging signal representing useful substrate information. As reflected in the bottom graph, the spurious emission noise peak 110 can then be suppressed or eliminated from consideration by manipulating the secondary electron signal $I_d$ data using the current $I_{ba}$ data collected by the screened beam-limiting aperture 50.
Figure 2:
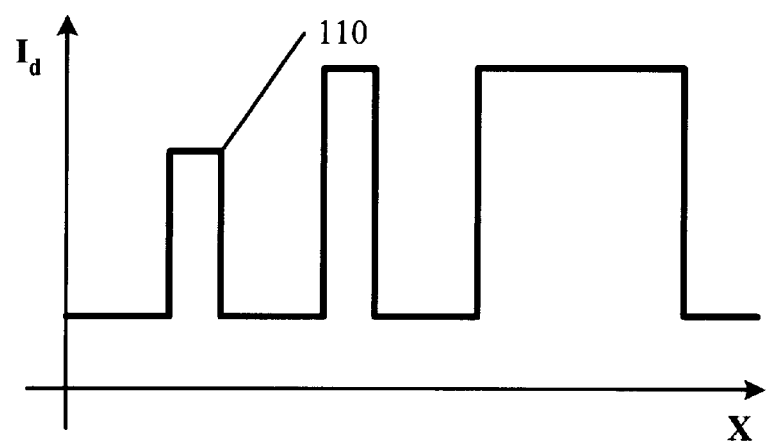
Figure 2:
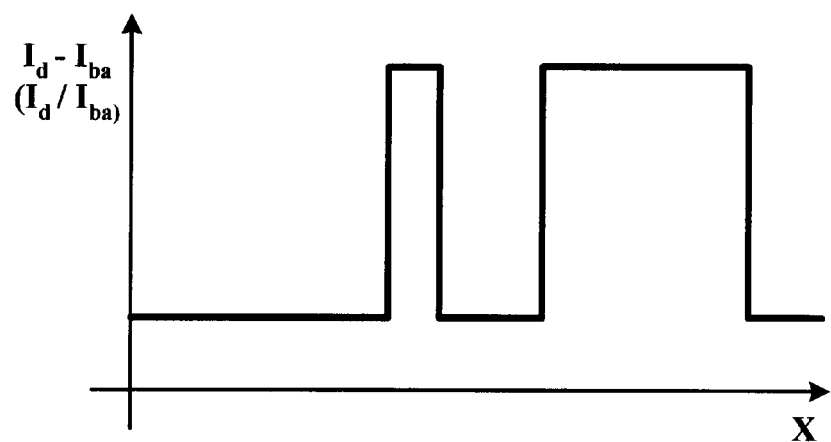

An implementation of the noise suppressing scheme is illustrated also in FIG. 2. The current $I_{ba}$ (top graph) collected by the screened beam-limiting aperture 50 shows an emission noise peak 100 made while the electron beam $I_b$ is scanned (for example along the x-axis) across the sample 90. The secondary electron signal $I_d$ (middle graph) includes an emission noise peak 110, superimposed on the imaging signal representing useful substrate information. This additional peak, due to the fluctuation in the emission current, could be interpreted as a substrate defect. The spurious emission noise peak 110 can then be suppressed or eliminated from consideration by processing the secondary electron signal $I_d$ data using the current $I_{ba}$ data collected by the screened beam-limiting aperture 50 (bottom graph). For example, the secondary electron signal $I_d$ may be divided by the current $I_{ba}$ collected by the beam-limiting aperture 50 or, alternatively, the current $I_{ba}$ collected by the beam-limiting aperture 50 may be subtracted from the secondary electron signal $I_d$. (If needed, prior to such subtraction or division, either or both of the electron signal $I_d$ data or the current $I_{ba}$ data may linearly transformed with a shift of the origin or multiplication by a scaling factor.) The correction of the secondary electron signal $I_d$ data to account for emission noise by using the current $I_{ba}$ data collected by the screened beam-limiting aperture 50 can be suitably carried out by a processor. The elimination of the effect of the emission noise increases the detection sensitivity of an inspection tool, in particular to defects smaller than the beam spot size. This allows the use of a larger spot size and the imaging of the substrate on a more coarse pixel grid. Such imaging in turn reduces the total number of required pixels and therefore increases the throughput of the tool.

The role of the screening aperture is crucial. If, for example, the current from the extractor electrode aperture or an un-screened beam-limiting aperture were used as a reference signal, the probability of noise suppression would be significantly reduced. This is due to the fact that the electron emission from the tip is strongly localized, and varies on a microscopic scale. Consequently, the electron beam varies spatially such that the noise in one part of the beam may be quite independent from the noise in a different part of the beam. The majority of the emitted electron current $I_e$, collected by the extraction electrode, includes thermal emission from the shank of the emitting tip, and is therefore not a sensitive measure of emission noise near the tip apex. Similarly, the current collected by an un-screened beam-limiting aperture contains emission from emitting regions that do not contribute to the beam current $I_b$. The electron current collected by the extraction electrode or an unscreened beam-limiting aperture has been used before as a means of trying to stabilize the emitted electron current using a direct feedback loop. This earlier approach did not prove practical, for the reasons described above. The use of a feedback loop to control the electrostatic field applied to the emitter has the further disadvantage of disturbing the dynamic equilibrium between electrostatic forces, surface migration and electron emission at the tip, which results in varying electron emission conditions and electron-optical properties.

The scope of the present invention is meant to be that set forth in the claims that follow and equivalents thereof, and is not limited to any of the specific embodiments described above.

What is claimed is:

1. A method for generating an electron beam, comprising the steps of:

generating an electron beam using a field emission emitter;

passing a first passed portion of said electron beam through a screening aperture defined by a screening element, said screening element collecting a first collected portion of said electron beam, wherein the first passed portion comprises only a portion of the electron beam comprising spatially correlated electrons;

passing a second passed portion of said electron beam through a beam-limiting aperture defined by a beam-limiting element, wherein said screening element is located between said emitter and said beam-limiting aperture and said beam-limiting element collects a second collected portion of said first passed electron beam portion incident thereon; and measuring the beam current at said beam-limiting element.

2. A method as recited in claim 1 wherein said screening aperture transmits only a portion of the electron beam within an emission half cone angle α given approximately by $$\alpha = \frac{2}{\sqrt{\pi}}\sqrt{\frac{kT}{\Phi}}$$

where T is the temperature of the tip of said emitter, k is Boltzmann's constant, and Φ is the electron energy.

3. An inspection method using a field emission electron gun, comprising the steps of:
  generating an electron beam using a field emission emitter;
  passing a first passed portion of said electron beam through a screening aperture defined by a screening element, said screening element collecting a first collected portion of said electron beam, wherein the first passed portion comprises only a portion of the electron beam comprising spatially correlated electrons;
  passing a second passed portion of said electron beam through a beam-limiting aperture defined by a beam-limiting element, wherein said screening element is located between said emitter and said beam-limiting aperture and said beam-limiting element collects a second collected portion of said first passed electron beam portion incident thereon;
  measuring the beam current at said beam-limiting element to generate beam current data;
  directing a final portion of said electron beam onto a surface of a target; and
  measuring the interaction of said final portion of the electron beam and said target to generate corrected target data by correcting for the effect of field emission noise using said beam current data.

4. A method as recited in claim 3 wherein said screening aperture transmits only a portion of the electron beam within an emission half cone angle α given approximately by $$\alpha = \frac{2}{\sqrt{\pi}}\sqrt{\frac{kT}{\Phi}}$$

where T is the temperature of the tip of said emitter, k is Boltzmann's constant, and Φ is the electron energy.

5. A method as recited in claim 3 wherein said step of measuring the interaction of said electron beam and said target includes measuring the emission of secondary electrons from said target.

6. A method as recited in claim 3 wherein said step of directing said final portion of the electron beam onto the surface of the target includes focusing said electron beam onto the surface of said target.

7. A method as recited in claim 3 further comprising the step of deflecting said final portion of the eletron beam so as to move said beam along the surface of said target.

8. An apparatus for generating an electron beam, comprising:
  a field emission emitter for generating an electron beam;
  a screening element in the path of said electron beam, the screening element defining a screening aperture in the path of the beam for allowing a first portion of the electron beam to pass therethrough, said screening element is adapted to collect a first collected portion of said electron beam, wherein said first passed portion comprises only a portion of the electron beam comprising spatially correlated electrons;
  a beam-limiting element in the path of said electron beam, said beam-limiting element defining a beam-limiting aperture for allowing a second passed portion of said electron beam to pass therethrough, wherein said screening element is located between said emitter and said beam-limiting aperture, said beam-limiting element is adapted to collect a second collected portion of said first passed electron beam portion incident thereon; and
  means for measuring the beam current at said beam-limiting element.

9. An apparatus as recited in claim 8 wherein said screening aperture transmits only a portion of the electron beam within an emission half cone angle α given approximately by $$\alpha = \frac{2}{\sqrt{\pi}}\sqrt{\frac{kT}{\Phi}}$$

where T is the temperature of the tip of said emitter, k is Boltzmann's constant, and Φ is the electron energy.

10. An apparatus for inspecting a target using a field emission electron gun, comprising:
  a field emission emitter for generating an electron beam;
  a screening element, defining a screening aperture, in the path of said electron beam, the screening aperture for allowing a first portion of the electron beam to pass therethrough, said screening element is adapted to collect a first collected portion of said electron beam, wherein the first passed portion comprises only a portion of the electron beam comprising spatially correlated electrons;
  a beam-limiting element in the path of said electron beam, said beam-limiting element defining a beam-limiting aperture for allowing a second passed portion of said electron beam to pass therethrough, wherein said screening element is located between said emitter and said beam-limiting aperture, said beam-limiting element is adapted to collect a second collected portion of said first passed electron beam portion incident thereon;
  means for measuring the beam current at said beam-limiting element;
  means for directing a final portion of said electron beam onto a surface of a target;
  a detector for measuring the interaction of said final portion of the electron beam and said target to generate corrected target data; and
  processor means for generating corrected target data by correcting for the effect of field emission noise using said beam current data.

11. An apparatus as recited in claim 10 wherein said screening aperture transmits only a portion of the electron beam within an emission half cone angle α given approximately by $$\alpha = \frac{2}{\sqrt{\pi}}\sqrt{\frac{kT}{\Phi}}$$

where T is the temperature of the tip of said emitter, k is Boltzmann's constant, and Φ is the electron energy.

12. An apparatus as recited in claim 10 wherein said detector is an electron detector for measuring the emission of secondary electrons from said target.

13. An apparatus as recited in claim 10 wherein said means for directing said final portion of the electron beam onto the surface of the target includes an electron-optic lens for focusing said electron beam onto the surface of said target.

14. An apparatus as recited in claim 10 further comprising means for deflecting said final portion of the electron beam so as to move said beam along the surface of said target.

15. A method as recited in claim 1, wherein the first collected electron beam portion collected by said screening element is substantially greater than the second collected electron beam portion collected by said beam-limiting element.

16. A method as recited in claim 3, wherein the first collected electron beam portion collected by said screening element is substantially greater than the second collected electron beam portion collected by said beam-limiting element.

17. An apparatus as recited in claim 8, wherein the first collected electron beam portion collected by said screening element is substantially greater than the second collected electron beam portion collected by said beam-limiting element.

18. An apparatus as recited in claim 10, wherein the first collected electron beam portion collected by said screening element is substantially greater than the second collected electron beam portion collected by said beam-limiting element.

* * * * *